US009339295B2

(12) United States Patent
Fung et al.

(10) Patent No.: US 9,339,295 B2
(45) Date of Patent: May 17, 2016

(54) PERICARDIAL ACCESS DEVICES AND METHODS

(71) Applicant: SentreHEART, Inc., Redwood City, CA (US)

(72) Inventors: Gregory W. Fung, Redwood Shores, CA (US); Arnold M. Escano, Santa Clara, CA (US); Randall J. Lee, Hillsborough, CA (US)

(73) Assignee: SentreHEART, INC., Redwood City, CA (US)

( * ) Notice: Subject to any disclaimer, the term of this patent is extended or adjusted under 35 U.S.C. 154(b) by 242 days.

(21) Appl. No.: 14/060,482

(22) Filed: Oct. 22, 2013

(65) Prior Publication Data
US 2014/0114337 A1    Apr. 24, 2014

Related U.S. Application Data

(60) Provisional application No. 61/717,022, filed on Oct. 22, 2012.

(51) Int. Cl.
*A61B 17/34* (2006.01)
*A61B 19/00* (2006.01)
*A61B 17/00* (2006.01)

(52) U.S. Cl.
CPC ... *A61B 17/3478* (2013.01); *A61B 2017/00247* (2013.01); *A61B 2019/303* (2013.01); *A61B 2019/306* (2013.01)

(58) Field of Classification Search
CPC ............... A61B 17/3476; A61B 2017/00243; A61B 2017/00247; A61B 2019/306; A61B 2019/305; A61B 2019/304
See application file for complete search history.

(56) References Cited

U.S. PATENT DOCUMENTS

| | | | |
|---|---|---|---|
| 3,685,509 A | 8/1972 | Bentall |
| 4,164,943 A | 8/1979 | Hill et al. |
| 4,222,382 A | 9/1980 | Antonsson et al. |
| 4,281,659 A | 8/1981 | Farrar et al. |
| 4,991,578 A | 2/1991 | Cohen |
| 4,995,866 A | 2/1991 | Amplatz et al. |
| 5,071,428 A | 12/1991 | Chin et al. |
| 5,226,890 A | 7/1993 | Ianniruberto et al. |
| 5,332,398 A | 7/1994 | Miller et al. |

(Continued)

FOREIGN PATENT DOCUMENTS

| | | | |
|---|---|---|---|
| CN | 102065781 A | 5/2011 |
| WO | WO-03/066147 A1 | 8/2003 |

(Continued)

OTHER PUBLICATIONS

International Search Report mailed on Jan. 14, 2014 for PCT Patent Application No. PCT/US2013/66104, filed on Oct. 22, 2013, two pages.

(Continued)

*Primary Examiner* — Jonathan W Miles
(74) *Attorney, Agent, or Firm* — Morrison & Foerster LLP

(57) ABSTRACT

Described here are devices and methods for accessing the pericardial space. The access devices may include a piercing member such as a needle and a proximal shoulder having a contact surface for contacting the pericardium as the piercing member pierces the pericardium. In some instances, the distance between the piercing member and the proximal shoulder may be adjustable.

20 Claims, 4 Drawing Sheets

(56) References Cited

U.S. PATENT DOCUMENTS

| | | | |
|---|---|---|---|
| 5,407,427 A | 4/1995 | Zhu et al. | |
| 5,695,504 A | 12/1997 | Gifford, III et al. | |
| 5,827,216 A | 10/1998 | Igo et al. | |
| 5,972,013 A | 10/1999 | Schmidt | |
| 6,231,518 B1 * | 5/2001 | Grabek | A61B 10/06 600/508 |
| 6,423,051 B1 | 7/2002 | Kaplan et al. | |
| 6,890,295 B2 * | 5/2005 | Michels | A61B 17/3415 600/114 |
| 6,918,890 B2 | 7/2005 | Schmidt | |
| 6,918,908 B2 * | 7/2005 | Bonner | A61B 18/1485 600/114 |
| 7,309,328 B2 | 12/2007 | Kaplan et al. | |
| 7,736,347 B2 | 6/2010 | Kaplan et al. | |
| 7,857,822 B2 | 12/2010 | Fleischman et al. | |
| 8,273,072 B2 | 9/2012 | Jahns et al. | |
| 8,282,565 B2 | 10/2012 | Mahapatra et al. | |
| 8,603,031 B2 * | 12/2013 | Callas | A61B 17/3478 604/115 |
| 8,628,552 B2 * | 1/2014 | Toy | A61M 5/3286 606/185 |
| 2002/0058925 A1 * | 5/2002 | Kaplan | A61B 17/3421 604/506 |
| 2004/0167558 A1 | 8/2004 | Igo et al. | |
| 2005/0165466 A1 | 7/2005 | Morris et al. | |
| 2005/0187545 A1 | 8/2005 | Hooven et al. | |
| 2006/0106442 A1 | 5/2006 | Richardson et al. | |
| 2007/0010708 A1 | 1/2007 | Ness | |
| 2007/0083194 A1 | 4/2007 | Kunis et al. | |
| 2007/0219546 A1 | 9/2007 | Mody et al. | |
| 2008/0294174 A1 | 11/2008 | Bardsley et al. | |
| 2009/0187074 A1 | 7/2009 | Saadat et al. | |
| 2010/0331854 A1 | 12/2010 | Greenberg et al. | |
| 2011/0077672 A1 | 3/2011 | Fleischman et al. | |
| 2012/0095434 A1 | 4/2012 | Fung et al. | |

FOREIGN PATENT DOCUMENTS

| | | |
|---|---|---|
| WO | WO-2009/120953 A2 | 10/2009 |
| WO | WO-2009/120953 A3 | 10/2009 |
| WO | WO-2011/130456 A1 | 10/2011 |

OTHER PUBLICATIONS

International Search Report mailed on Jul. 1, 2011, for PCT Patent Application No. PCT/US2011/032382, filed on Apr. 13, 2011, 2 pages.

Ling, L.H. et al. (May 1997). "Pericardial Thickness Measured with Transesophageal Echocardiography: Feasibility and Potential Clinical Usefulness," *J. Am. Coll. Cardiol.* 29(6):1317-1323.

Non-Final Office Action mailed on Nov. 22, 2000 for U.S. Appl. No. 09/397,392, filed Sep. 16, 1999, 3 pages.

Non-Final Office Action mailed on Sep. 21, 2009 for U.S. Appl. No. 11/873,228, filed Oct. 16, 2007, 8 pages.

Non-Final Office Action mailed on Jul. 9, 2003 for U.S. Appl. No. 10/002,329, filed Nov. 1, 2001, 7 pages.

Non-Final Office Action mailed on Mar. 22, 2005 for U.S. Appl. No. 10/002,329, filed Nov. 1, 2001, 7 pages.

Non-Final Office Action mailed on Jun. 29, 2005 for U.S. Appl. No. 10/002,329, filed Nov. 1, 2001, 7 pages.

Non-Final Office Action mailed on Oct. 3, 2005 for U.S. Appl. No. 10/002,329, filed Nov. 1, 2001, 8 pages.

Non-Final Office Action mailed on Mar. 26, 2014 for U.S. Appl. No. 13/086,328, filed Apr. 13, 2011, 8 pages.

Notice of Allowance mailed on Jul. 16, 2001 for U.S. Appl. No. 09/397,392, filed Sep. 16, 1999, 2 pages.

Notice of Allowance mailed on Jan. 29, 2010 for U.S. Appl. No. 11/873,228, filed Oct. 16, 2007, 4 pages.

Notice of Allowance mailed on Jan. 28, 2004 for U.S. Appl. No. 10/002,329, filed Nov. 1, 2001, 4 pages.

Notice of Allowance mailed on Jul. 16, 2007 for U.S. Appl. No. 10/002,329, filed Nov. 1, 2001, 4 pages.

Restriction Requirement mailed on Aug. 11, 2000 for U.S. Appl. No. 09/397,392, filed Sep. 16, 1999, 6 pages.

Written Opinion of the International Searching Authority mailed on Jan. 14, 2014 for PCT Patent Application No. PCT/US2013/66104, filed on Oct. 22, 2013, six pages.

Written Opinion of the International Searching Authority mailed on Jul. 1, 2011, for PCT Patent Application No. PCT/US2011/032382, filed on Apr. 13, 2011, 5 pages.

* cited by examiner

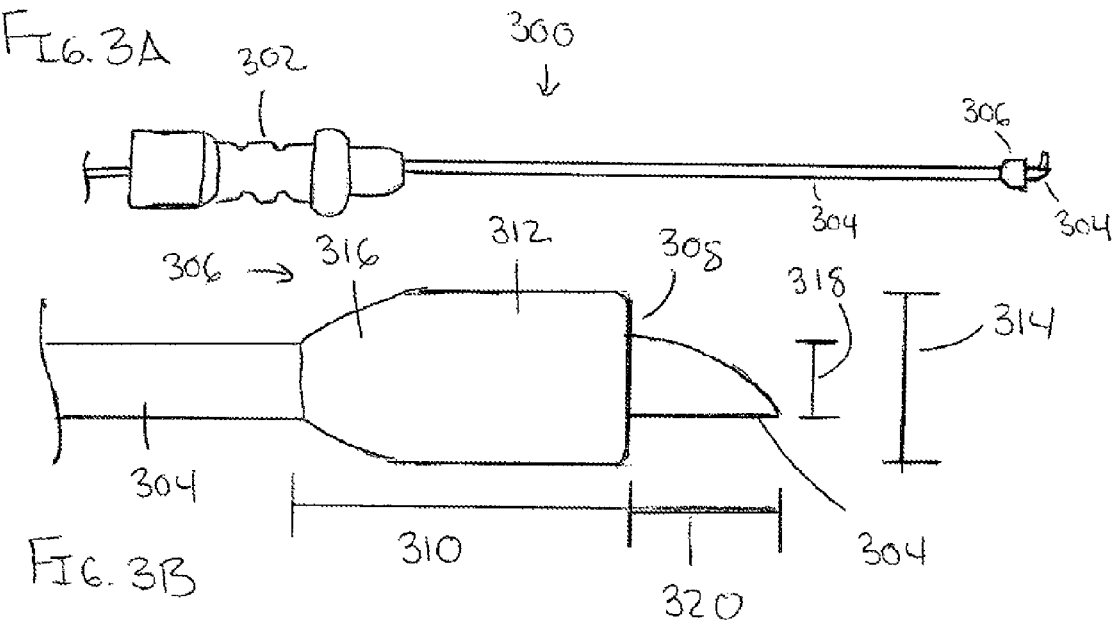
FIG. 3A
FIG. 3B
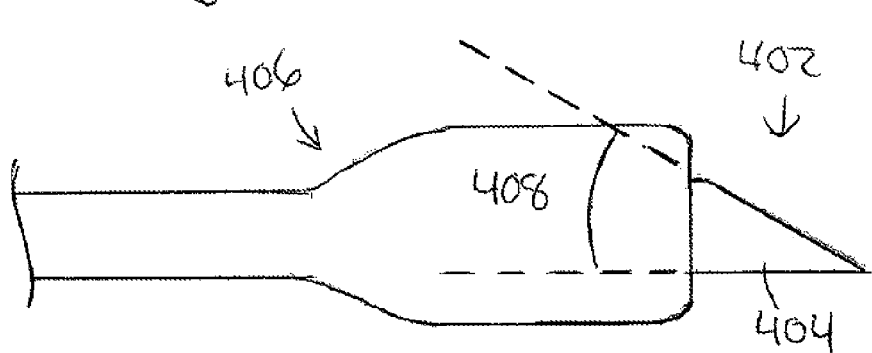
FIG. 4
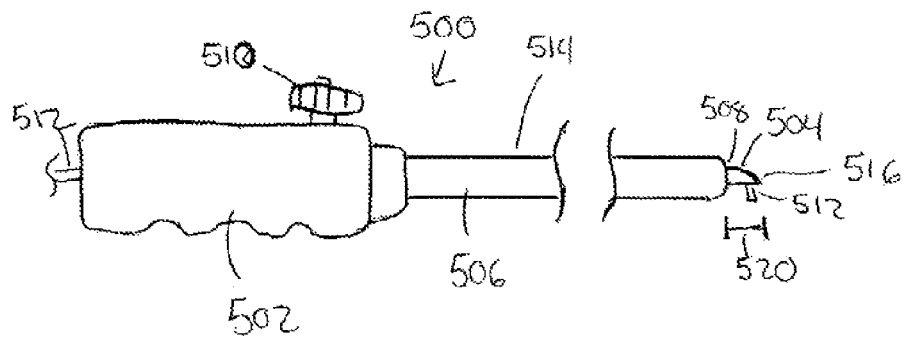
FIG. 5

PERICARDIAL ACCESS DEVICES AND METHODS

CROSS-REFERENCE TO RELATED APPLICATIONS

This application claims priority to U.S. provisional patent application Ser. No. 61/717,022, filed Oct. 22, 2012 and titled "PERICARDIAL ACCESS DEVICES AND METHODS," the content of which is hereby incorporated by reference in its entirety.

FIELD

Described here are devices and methods for gaining access to the pericardial space through the pericardium.

BACKGROUND

Access to internal and external structures of the heart may be desirable for the treatment of cardiovascular disease. In some cases, the treatment may involve the delivery of devices to the heart. One way in which a heart may be accessed for device delivery is by an intravascular approach. Intravascular pathways to the heart may involve advancing the device from a femoral vein to the vena cava, through which the chambers and valves of the right side of the heart (e.g., right atrium, right ventricle, etc.) may be accessed. The left side of the heart may also be accessed from this approach by using a transseptal procedure. Alternatively, the left atrium and left ventricle may be intravascularly accessed by a retrograde pathway from the aorta.

However, intravascular access to the heart may not be ideal in all circumstances, such as for the delivery of larger devices, and especially if external structures of the heart are targeted. In such circumstances, the heart may also be accessed through an opening or puncture in the pericardium, which may provide direct access to the external (epicardial) surface of the heart. Accessing the heart via a non-effused pericardium is becoming a recognized access route to the heart. The ability to access the heart via a non-vascular pathway may be useful for a variety of applications, including device or drug delivery, left atrial appendage exclusion, ablation of fibrillating tissue, placement of leads, and the like. Despite these benefits, puncturing the pericardium without contacting and/or damaging the heart itself may prove to be a challenge. Current methods that attempt to reduce this risk involve grasping and/or suctioning the pericardium prior to puncturing it, but the presence of epicardial fat and other irregularities may prevent direct access to the pericardium. In some cases, highly trained physicians may be able to pierce the pericardium without piercing the heart by carefully advancing a needle towards the heart. They may rely on tactile feedback to avoid puncturing the heart, and use this tactile feedback to accommodate and/or compensate for the displacement of the heart and pericardium during a beating heart procedure. However, advancing conventional needles to the heart by tactile feedback may be particularly risky for inexperienced physicians, as these conventional needles may be accidentally advanced into the heart. Additional methods and devices for accessing the pericardial space are desirable.

BRIEF SUMMARY

Described here are systems, devices and methods for accessing the pericardial space through the pericardium. In some variations, a system may comprise an access device having a piercing member and a proximal shoulder, the proximal shoulder having a distal contact surface with an outer diameter larger than the outer diameter of the piercing member. In some of these variations, the piercing member may extend distally a first distance beyond the distal contact surface. In some of these variations, the first distance may be adjustable. In other variations, the first distance may be fixed. In some variations, the first distance may be between about 1 mm and 6 mm. In some of these variations, the first distance may be between about 3 mm and 5 mm. In some of these variations, the first distance may be about 4.0 mm. As used herein, "about" means±5%. The distal contact surface may be positioned approximately perpendicular to a longitudinal axis to the piercing member.

In some variations, the piercing member may comprise a needle. In some of these variations, the needle may comprise a Tuohy needle. In others of these variations, the needle may comprise a beveled needle. The needle may have any suitable outer diameter. In some variations, the needle may be a 17 gauge needle. In some of these variations, the distal contact surface may have an outer diameter of about 0.13 inches. In some variations, the proximal shoulder may comprise a sleeve. In some of these variations, the sleeve may be fixed to a piercing member comprising a needle. In others of these variations, the sleeve may be moveable relative to a piercing member comprising a needle. In some variations, the system may further comprise a guide wire. In some of these variations, the guide wire may be advanced from a proximal portion of the access device and out of an opening in the piercing member. In some variations, the system may further comprise a trocar and cannula, wherein the trocar may be used to place a portion of the cannula within the body, and the access device may be advanced through the cannula.

Also described here are methods for accessing the pericardial space. In some variations, the methods may comprise advancing a distal portion of an access device to the pericardium, the access device comprising a piercing member and a proximal shoulder, the proximal shoulder comprising a distal contact surface having an outer diameter greater than an outer diameter of the piercing member, wherein the piercing member extends distally a first distance beyond the distal contact surface, engaging the pericardium with the piercing member, piercing the pericardium with the piercing member, and advancing the access device to engage the pericardium with the distal contact surface of the access device. In some of these variations, the method may further comprise advancing a distal portion of a guide wire into the pericardial space through an opening in the piercing member. In some of these variations, the piercing member may comprise a needle. In some of these variations, the needle may comprise a Tuohy needle.

BRIEF DESCRIPTION OF THE DRAWINGS

FIGS. 3A, 3B and 4 depict side views of illustrative variations of the access devices described here.

FIG. 5 depicts a side view of a variation of the access devices having an adjustment mechanism.

DETAILED DESCRIPTION

Figure 1:
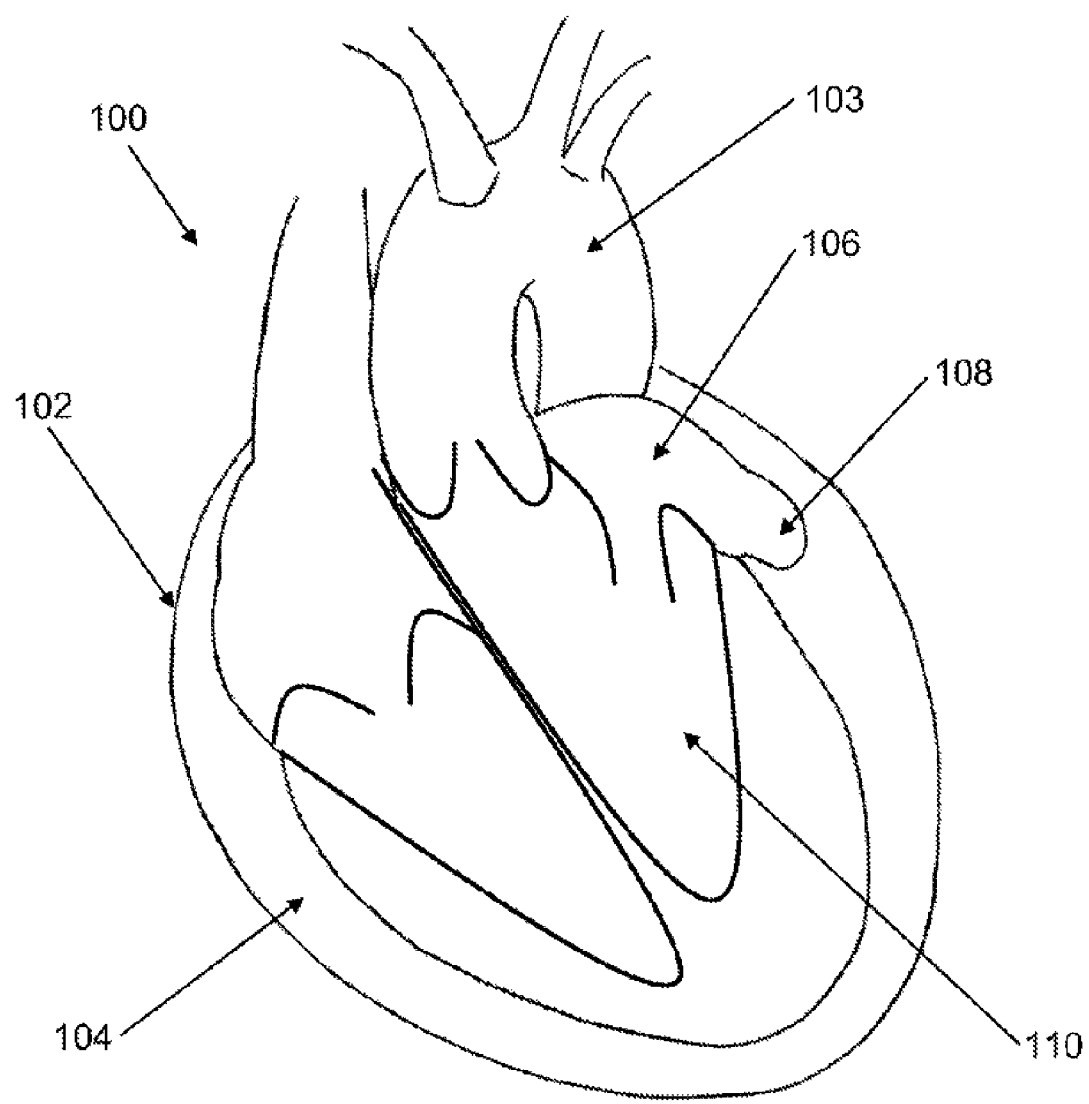
FIG. 1 depicts typical anatomy of the heart and pericardium.

Described here are devices and methods for accessing the pericardial space through the pericardium. The pericardium is a tough membrane that surrounds the heart. FIG. 1 depicts a heart (100) enclosed by a pericardium (102). FIG. 1 also depicts various anatomical structures of the heart, including the left atrium (106), left atrial appendage (108), left ventricle (110), and the aortic arch (103). The pericardium (102) may be filled with a fluid that may separate it from the heart. The space between the pericardium (102) and heart (100) is the pericardial space (104). The distance between the pericardium and the surface of the heart may vary. For example, the pericardium may be about 5 millimeters away from heart in some areas, while the pericardium may directly contact the heart (100) in other areas. While the devices and methods described here are described in reference to puncturing the pericardium to provide access to the heart, it should be understood that these devices and methods may be used to create a puncture in or otherwise facilitate access to any fluid-filled membrane or sac to access the structures therein, e.g., dura mater, peritoneum, amniotic sac, etc.

Devices

Generally, the devices described here comprise a piercing member and a proximal shoulder having a distal contact surface. The distal contact surface of the proximal shoulder may engage the pericardium as the distal tip pierces the pericardium, and may help minimize the risk that the piercing member punctures or otherwise damages the heart as it is advanced through the pericardium, as will be described in more detail below. The piercing member may comprise a needle or the like, and in some instances may comprise one or more lumens passing at least partially therethrough. The lumen may be used to introduce a guide wire into the pericardial space through the pericardium, as will be described in more detail below.

Figure 2A:
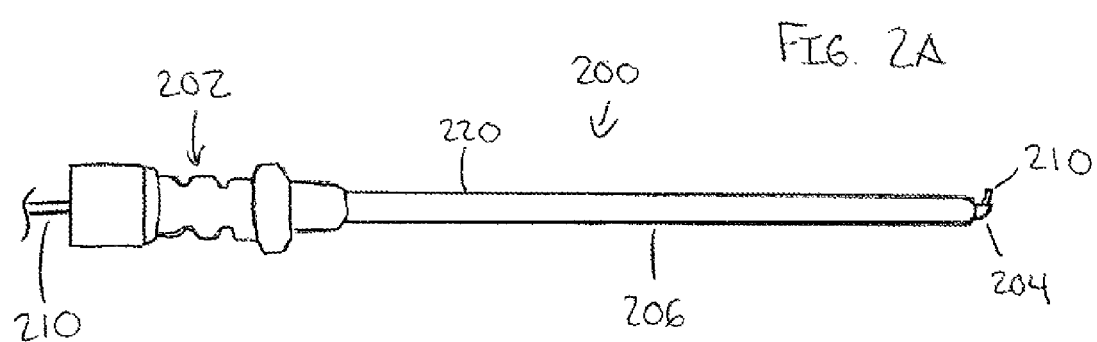
FIG. 2A depicts a side view a variation of the access devices described here.
Figure 2B:
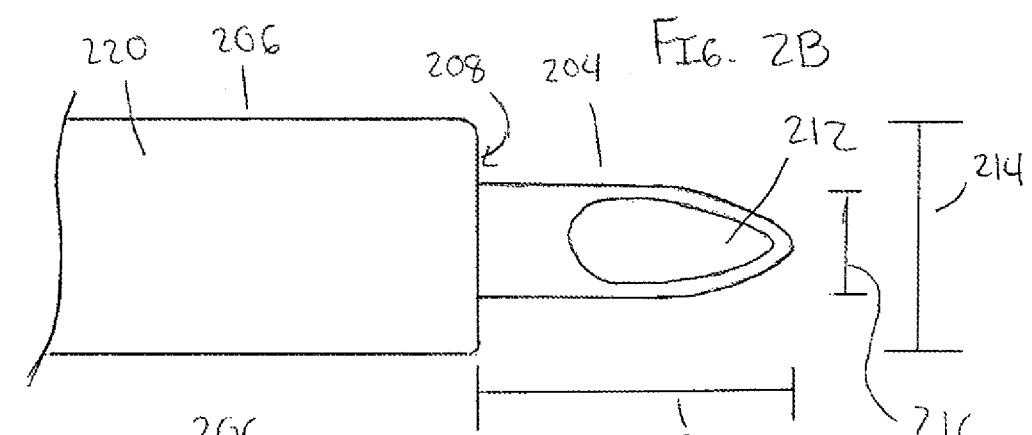
FIGS. 2B and 2C depict a top view and a side view, respectively, of the access device shown in FIG. 2A
Figure 2C:
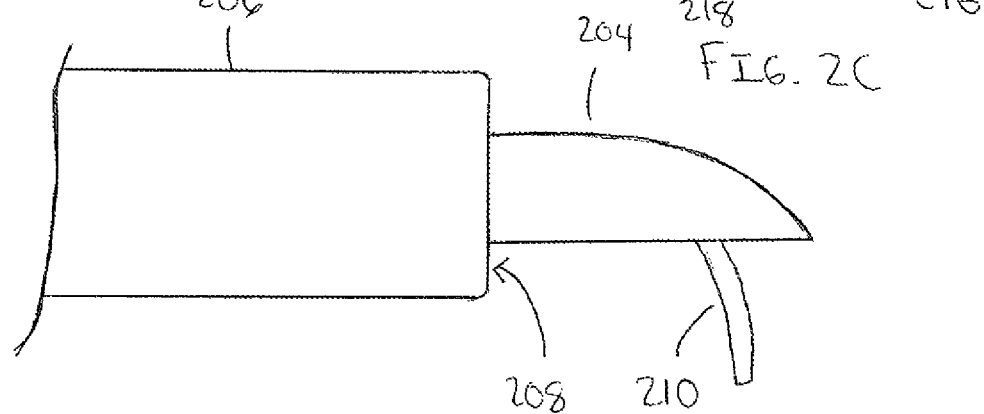

FIGS. 2A-2C depict an illustrative variation of the access devices described here. As shown in a side view in FIG. 2A, the access device (200) may comprise a handle (202), a piercing member (204), and proximal shoulder (206). FIGS. 2B and 2C show a top view and a side view, respectively, of a distal portion of the access device (200). As shown there, the distal end of the proximal shoulder (206) may form a distal contact surface (208) that may contact the pericardium, as will be described in more detail below. The distal contact surface (208) is generally flat, although it should be appreciated that in some variations the distal contact surface (208) may be patterned or textured. In the variation shown in FIGS. 2A-2C, the distal contact surface (208) may be positioned approximately perpendicularly to the longitudinal axis of the piercing member (204), but it should be appreciated that in some variations the distal contact surface (208) may be disposed at other angles relative to the longitudinal axis of the piercing member (204). For example, in some variations the distal contact surface (208) may be positioned 90 degrees relative to the longitudinal axis of the piercing member (204) or may be positioned between 85 and 95 degrees relative to the longitudinal axis of the piercing member (204). Also shown in FIGS. 2A and 2C is a guide wire (210), which may be introduced into a proximal portion of the access device (200) and advanced such that a distal portion of the guide wire (210) extends out of an opening (212) in a distal portion of the piercing member (204). Although not shown in FIGS. 2A-2C, it should be appreciated that the access devices described here may comprise one or more curves or bends along the length thereof.

Generally, the proximal shoulder (206) and corresponding distal contact surface (208) have a larger outer diameter (214) than the outer diameter (216) of the piercing member (204), and may be positioned relative to the piercing member (204) such that a distance (218) of the piercing member (204) extends distally beyond the proximal shoulder (206). In use, the access device (200) may be advanced relative to the heart such that piercing member (204) engages the pericardium (not shown). The access device (200) may be further advanced to push the piercing member (204) against the pericardium, but the tough nature of the pericardium may prevent the piercing member (204) from piercing the pericardium until the force applied to the access device (200) reaches a certain level. When the piercing member (204) does pierce the pericardium, the increased force applied to the access device (e.g., by the user) may cause the access device (200) to suddenly advance relative the pericardium. When conventional needles are used to puncture the pericardium in this way, a user may not be able stop forward movement of the needle in time to prevent the needle from puncturing the myocardium. Conversely, when the piercing member (204) of access device (200) punctures the pericardium, the force applied to the access device (200) may cause the access device (200) to advance until the contact surface (208) of proximal shoulder (206) engages the pericardium. This engagement may resist further advancement of the access device (200), which may reduce the likelihood the access device (200) is advanced far enough to puncture or otherwise damage the myocardium. In some variations, the edges of the distal contact surface (208) may be chamfered or rounded to reduce the likelihood that the edges puncture or pierce the pericardium when the contact surface (208) engages the pericardium. Additionally, in instances where the proximal shoulder (206) is accidentally advanced through the pericardium, the proximal shoulder (206) may contact the myocardium which may help deflect the access device (200) to angle the piercing member (204) away from the myocardium.

When the piercing member (204) punctures the pericardium, the access device (200) may be advanced up to the distance (218) before the pericardium engages the distal contact surface (208). Accordingly, the distance (218) that the piercing member (204) extends beyond the distal contact surface (208) may be configured such that access device (200) is advanced far enough during puncture to position the opening (212) within the pericardial space (e.g., so that a guide wire (210) may be advanced into the pericardial space), but not far enough to cause the piercing member (204) to puncture the myocardium. For example, in some variations the proximal shoulder (206) may be positioned such that the distance (218) is less than about 10 mm. In some variations, the proximal shoulder (206) may be positioned such that the distance (218) is between about 1 mm and about 6 mm. In some of these variations, the proximal shoulder (206) may be positioned such that the distance (218) is between about 3 mm and about 5 mm. In some of these variations, the proximal shoulder (206) may preferably be positioned such that the distance (218) is between about 3.5 mm and about 4.5 mm. In some of these variations, the proximal shoulder (206) may preferably be positioned such that distance (218) is about 4.0 mm. In some variations, the position of proximal shoulder (206) may be fixed relative to the position of the piercing member (204) such that the distance (218) is fixed. In other variations, as will be described in more detail below, the proximal shoulder may be moveable relative to the piercing member to adjust the exposed distance (218).

The piercing member (204) and proximal shoulder (206) may have any suitable diameters. For example, in some variations, the piercing member (204) may be a 17 gauge needle (e.g., having an outer diameter (216) of about 0.058 inches (about 1.47 mm)). In some of these variations, the outer diameter (214) of the proximal shoulder (206) may be between about 0.11 inches (about 2.79 mm) and about 0.17 inches (about 4.32 mm). In some of these variations, the proximal shoulder (206) may have an outer diameter (214) between about 0.12 inches (about 3.5 mm) and about 0.16 inches (about 4.06 mm). In some of these variations, the outer diameter (214) of the proximal shoulder (206) may be about 0.16 inches (about 4.06 mm). In others of these variations, the outer diameter (214) of the proximal shoulder (106) may be about 0.13 inches (about 3.30 mm). In other variations, the piercing member (204) may have an outer diameter (216) between about 0.02 inches (about 0.51 mm) and about 0.08 inches (about 2.03 mm). In some variations, the piercing member (204) may be a 22 gauge member (e.g. 0.028 inches (0.71 mm)). In some of these variations, the outer diameter (214) of the proximal shoulder may be between about 0.06 inches (about 1.52 mm) and about 0.14 inches (about 3.56 mm), or may be about 0.1 inches (about 2.54 mm).

In some variations, it may be desirable to have an outer diameter (214) of the proximal shoulder (206) that is at least a certain amount larger than the outer diameter (216) of the piercing member (204). For example, in some variations, the outer diameter (214) of the proximal shoulder (206) is at least 0.06 inches (1.52 mm) larger than the outer diameter (216) of the piercing member (204). For example, in some variations where the outer diameter (216) of the piercing member (204) is about 0.058 inches (about 1.47 mm), the outer diameter (214) of the proximal shoulder (206) may be at least about 0.118 inches (about 3.00 mm). In variations where the outer diameter (216) of the piercing member (204) is about 0.028 inches (about 0.71 mm), the outer diameter (214) of the proximal shoulder (206) may be at least about 0.088 inches (about 2.24 mm).

In some variations of the access devices described here, the proximal shoulder and piercing member may be formed separately and joined together. In other variations, the proximal shoulder and piercing member may be formed as a single component. Generally, the proximal shoulder may extend proximally along the piercing member from the distal contact surface toward the handle. In some variations, the proximal shoulder may extend from the distal contact surface to the handle of the access device. For example, in the variation of access device (200) shown in FIG. 2A-2C, the proximal shoulder (206) may comprise a sleeve (220), the proximal end of which may be connected to the handle (202) and the distal end of which may form the distal contact surface (208). While shown in FIGS. 2A-2C as having a constant outer diameter (216), it should be appreciated that in some variations, the diameter (216) of the proximal shoulder (206) may vary proximal to the distal contact surface (208). For example, in some variations it may be desirable to reduce the outer diameter of the proximal shoulder (206) proximally of the distal contact surface (208). Generally, the presence of the proximal shoulder (206) may increase the stiffness of the access device, which may reduce the tactile feedback a user may receive while advancing and manipulating the access device. Reducing the outer diameter of portions of the proximal shoulder (206), however, may increase the flexibility of the proximal shoulder, which may provide for more tactile feedback to a user.

In other variations, the proximal shoulder of the access device may extend along only a portion of the piercing member. In these variations, the limited length of the proximal shoulder may increase the flexibility of the access device, which may provide tactile feedback to a user as described above. For example, FIGS. 3A and 3B show another variation of an access device (300), comprising a handle (302), a piercing member (304), and a proximal shoulder (306) having a distal contact surface (308). The proximal shoulder (306) may extend proximally along the piercing member (304) from the distal contact surface (308) for a length (310). The length (310) may be any suitable value (e.g., about 10 mm, between about 5 mm and about 15 mm, or the like). In some variations, the length (310) may be less than 20 mm. In some of these variations, the length (310) may be preferably less than 15 mm. In some of these variations, the length (310) may be about 10 mm. Any of these lengths (310) may be used with any of the dimensions for the outer diameter of the proximal shoulder, the outer diameter of the piercing member, and the distance that the piercing member may extend from proximal shoulder described above with respect to FIGS. 2A-2C above. In some of these variations, the proximal shoulder (306) may be a sleeve that extends along only a portion of the piercing member (304). In some variations, the diameter of the proximal shoulder (306) may be constant along the length (310). In other variations, the proximal shoulder (306) may comprise a first portion (312) having an outer diameter (314), and a tapered portion (316) with an outer diameter that tapers between the outer diameter (314) of the first portion and the outer diameter (318) of the piercing member (304). The proximal shoulder (306) may be positioned such that the piercing member (304) extends beyond the distal contact surface (308) by a distance (320). The distance (320), as well as the outer diameters (314) and (318) of the proximal shoulder (306) and the piercing member (304) may be any suitable values, such as described in more detail above.

The piercing members of the access devices described here may comprise any suitable piercing member. In some variations, the piercing member may comprise a needle. In variations in which the piercing member comprises a needle, the needle may preferably be a Tuohy needle (such as shown in FIGS. 2A-2C and FIGS. 3A-3B), however the piercing member may comprise any suitable needle (e.g., a beveled needle, a domed needle, a cone-tipped needle, or the like). In variations where the needle comprises a Tuohy needle, the slight curve at the tip of the Tuohy needle may reduce the likelihood that the needle may puncture or otherwise damage the myocardium as it is advanced through the pericardium. The needle may be any suitable gauge (e.g., 17 gauge, 20 gauge, between 16 and 24 gauge, etc.).

FIG. 4 shows the distal end of an access device (400) having a piercing member (402) comprising a beveled needle (404). The access device (400) may additionally comprise a handle (not shown) and a proximal shoulder (406), such as described in more detail above. The beveled needle (404) may have a bevel angle (408). Bevel angle (408) may have any suitable value. For example, in some variations, bevel angle (408) may be between about 10 degrees and about 45 degrees. In some of these variations, the bevel angle may be about 15 degrees. In others of these variations, the bevel angle may be about 20 degrees. In still others of these variations, the bevel angle may be about 25 degrees. In yet others of these variations, the bevel angle may be about 30 degrees.

As mentioned above, in some variations the access devices described here may be configured such that the proximal shoulder is moveable relative to the piercing member to adjust the distance that the piercing member extends beyond a distal contact surface of the proximal shoulder. For example, FIG. 5 shows one such variation of an adjustable access device (500). As shown there, the access device (500) may comprise a handle (502), a piercing member (504), and a proximal shoulder (506) having a distal contact surface (508). The handle (502) may further comprise an adjustment control (510), which may adjust the relative positioning of the distal contact surface (508) of the proximal shoulder (506) and the piercing member (504). In some variations, the access device (500) may be used with a guide wire (512), which may be introduced into a proximal portion of the access device (500) and advanced such that a portion of the guide wire (512) extends out of an opening (not shown) in a distal portion of the piercing member (504).

When an adjustable access device (such as the access device (500) shown in FIG. 5) comprises an adjustment control, the adjustment control may be any suitable mechanism (e.g., a button, knob, lever, or the like) that allows a user to adjust the relative positioning of the proximal shoulder and the piercing member. For example, in the variation of the adjustable access device (500) shown in FIG. 5, the proximal shoulder (506) may comprise a sleeve (514) operatively attached to the handle (502), and the piercing member (504) may comprise a needle (516) positioned within the sleeve (514) and operatively attached to the handle (502). In some variations, actuation of the adjustment control (510) may move the sleeve (514) relative to the handle (502) and the needle (516). In these variations, the sleeve (514) may be advanced using the adjustment control (510) to decrease the length (520) of the piercing member (504) that extends beyond the distal contact surface (508), and may be retracted using the adjustment control (510) to increase the length (520) of the piercing member (504) that extends beyond the distal contact surface (508). In other variations, actuation of the adjustment control (510) may move the needle (516) relative to the handle (502) and the sleeve (514). In these variations, the needle (516) may be advanced using the adjustment control (510) to increase length of the piercing member (504) that extends beyond the distal contact surface (508), and may be retracted using the adjustment control (510) to decrease the length of the piercing member (504) that extends beyond the distal contact surface (508). It should be appreciated that in some variations, the relative position between the piercing member (504) and the proximal shoulder (502) may be fixed or otherwise locked when adjustment control (510) is not be actuated, which may help prevent inadvertent movement between the piercing member (504) and the proximal shoulder (506) in use of the access device (500).

As mentioned above, the dimensions of the piercing member and proximal shoulder may be any combination of the dimensions listed above. For example, in some variations, the piercing member may have an outer diameter of about 0.058 inches (about 1.47 mm), and the proximal shoulder may have an outer diameter of at least about 0.118 inches/3.00 mm (e.g., about 0.12 inches/3.05 mm, about 0.13 inches/3.30 mm). In some of these variations the piercing member may extend from the proximal shoulder by a distance between about 1 mm and about 6 mm. In some of these variations, the piercing member may extend from the proximal shoulder by a distance between about 3 mm and about 5 mm. It should be appreciated that in some instances this distance may be adjustable. The length of the proximal shoulder may extend to a handle of a device, or may be any of the lengths described above (e.g., less than 20 mm, less than 15 mm, between about 5 mm and about 15 mm, about 10 mm).

In other variations, the piercing member may have an outer diameter of about 0.028 inches (about 0.71 mm), and the proximal shoulder may have an outer diameter of at least about 0.088 inches/2.24 mm or between about 0.06 inches (about 1.52 mm) and about 0.14 inches (about 3.56 mm). In some of these variations the piercing member may extend from the proximal shoulder by a distance between about 1 mm and about 6 mm. In some of these variations, the piercing member may extend from the proximal shoulder by a distance between about 3 mm and about 5 mm. It should be appreciated that in some instances this distance may be adjustable. The length of the proximal shoulder may extend to a handle of a device, or may be any of the lengths described above (e.g., less than 20 mm, less than 15 mm, between about 5 mm and about 15 mm, about 10 mm).

Methods

Figure 6A:
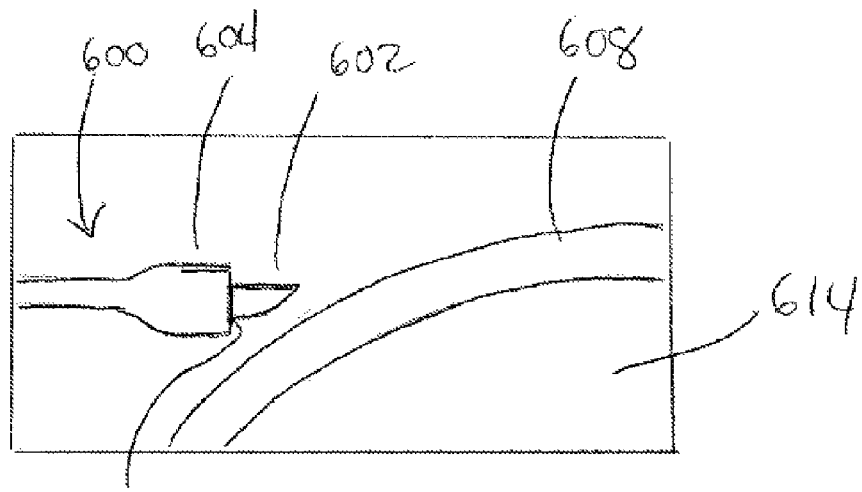
FIGS. 6A-6C depict a illustrative method of accessing the pericardial space using the access devices described here.
Figure 6B:
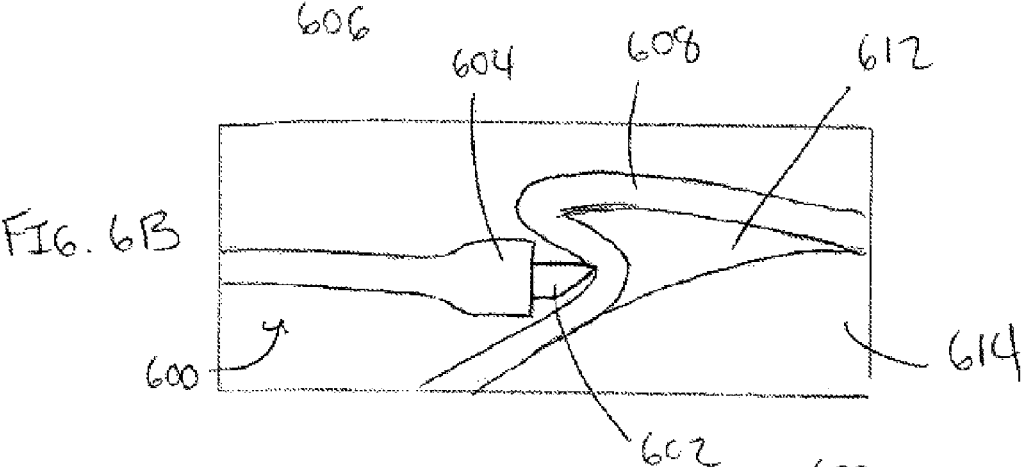
Figure 6C:
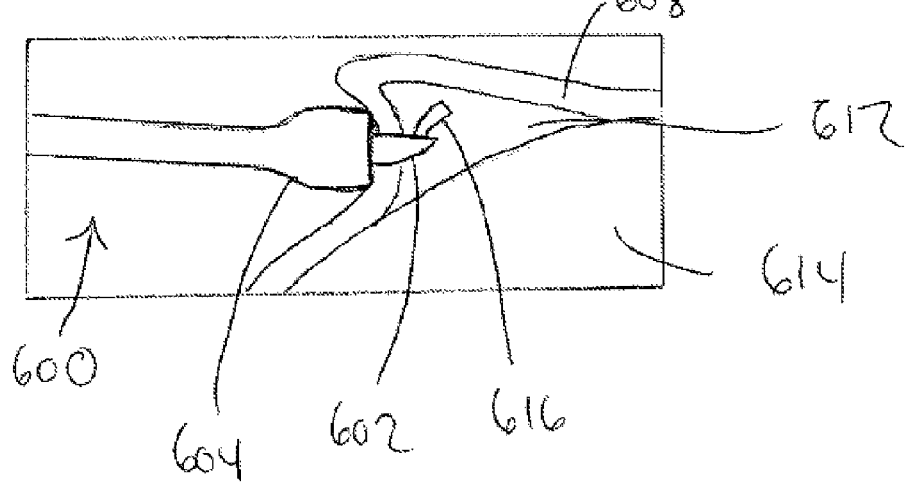

The access devices described above may be used to pierce the pericardium or other fluid-filled membrane or sac (e.g., dura mater, peritoneum, amniotic sac, etc.) to access the structures therein. Generally, the methods described here comprise advancing an access device to engage the membrane with a piercing member, applying a force to membrane with the piercing member to pierce the membrane, and advancing the access device to engage the membrane with the distal contact surface of a proximal shoulder. For example, FIGS. 6A-6C depict a method by which an access device (600) may be used to access the pericardial space of a patient. As shown there, access device (600) may comprise a piercing member (602) and a proximal shoulder (604) having a contact surface (606), though it should be appreciated that these components may be configured in any manner as described above. Access device (600) may be advanced to position the piercing member (602) near the pericardium (608), as shown in FIG. 6A. In some of these variations, the access device (600) may be advanced through a cannula (not shown), which may be placed in the body using a trocar or the like. The access device (600) may be manipulated to engage the pericardium (608) with the piecing member (602). The access device (600) may be further advanced to increase the force applied by the piercing member (602) to the pericardium. As the force applied by the piercing member (602) against the pericardium (608) increases, the pericardium (608) may be begin to tent, as shown in FIG. 6B. A user may incrementally increase the force applied by the piercing member (602) until the piercing member (602) punctures the pericardium (608). As the piercing member (602) punctures the pericardium, the force applied to the access device (600) to tent the pericardium (608) may cause the piercing member (602) to advance relative to the pericardium (610) until the contact surface (606) of the proximal shoulder (604) engages the pericardium (610), as shown in FIG. 6C, which may help stop advancement of the access device (600). When the distal contact surface (606) engages the pericardium (608), an opening (not shown) in the piercing member (602) may be positioned in the pericardial space (612) between the pericardium (608) and the myocardium (614). In some variations, a contrast agent may be delivered into the pericardial space (612) to confirm positioning of the positioning of the piercing member (604) (e.g., via fluoroscopic or other visualization techniques). In some variations, a distal portion of a guide wire (616) may be advanced out of the opening and into the pericardial space (612), and the access device (600) may be withdrawn to leave the distal portion of the guide wire (616) in place in the pericardial space.

In variations where the proximal shoulder (604) is moveable relative to the piercing member (602), the methods described above may comprise advancing the piercing member (602) relative to the proximal shoulder (604) (or retracing the proximal shoulder (604) relative to the piercing member (602)) when the access device (600) engages the pericardium (610). For example, the access device (600) may be advanced with the piercing member (602) in a fully- or partially-retracted position. This may help reduce the risk that the piercing member (602) catches on or otherwise damages tissue while being advanced toward the pericardium. Once the access device (600) has tented the pericardium, as shown in FIG. 6B, a user may increase the length of the piercing member (602) that extends beyond the contact surface (606) of the proximal shoulder (604). Additionally or alternatively, a user may increase the length of the piercing member (602) that extends beyond the distal contact surface (606) of the proximal shoulder (604) after the piercing member (602) has punctured the pericardium to further advanced the piercing member (602) into the pericardial space.

We claim:

1. A method of accessing a pericardial space between a pericardium and a heart, the method comprising:
   advancing a distal portion of an access device to the pericardium, the access device comprising a piercing member and a proximal shoulder, the proximal shoulder comprising a distal contact surface having an outer diameter greater than an outer diameter of the piercing member, wherein the piercing member extends distally a first distance beyond the distal contact surface;
   engaging the pericardium with the piercing member to tent the pericardium;
   piercing through the tented pericardium with the piercing member; and
   advancing the access device to engage the pericardium with the distal contact surface of the access device.

2. The method of claim 1 further comprising advancing a distal portion of a guide wire into the pericardial space through an opening in the piercing member.

3. The method of claim 2 further comprising withdrawing the access device while the distal portion of the guide wire remains in the pericardial space.

4. The method of claim 1 wherein the piercing member comprises a needle.

5. The method of claim 4 wherein the needle comprises a Tuohy needle.

6. The method of claim 4 wherein the needle is a 17 gauge needle.

7. The method of claim 1 wherein the position of the proximal shoulder is fixed relative to the position of the piercing member.

8. The method of claim 1 wherein the access device comprises a length between a proximal end and a distal end of the access device, and wherein the access device comprises a curve along its length.

9. The method of claim 1 wherein the first distance is adjustable.

10. The method of claim 9 wherein the access device further comprises a handle comprising an adjustment control configured to adjust the first distance.

11. The method of claim 9 wherein engaging the pericardium with the piercing member comprises advancing the piercing member relative to the proximal shoulder.

12. The method of claim 9 wherein engaging the pericardium with the piercing member comprises retracting the proximal shoulder relative to the piercing member.

13. The method of claim 9 wherein advancing a distal portion of an access device to the pericardium comprises advancing the access device with the piercing member in an at least partially retracted position.

14. The method of claim 9 further comprising increasing the first distance after the piercing member has pierced through the pericardium.

15. The method of claim 1 wherein the first distance is between about 1 mm and 6 mm.

16. The method of claim 15 wherein the first distance is between about 3 mm and 5 mm.

17. The method of claim 16 wherein the first distance is about 4.0 mm.

18. The method of claim 1 wherein the distal contact surface is approximately perpendicular to a longitudinal axis of the piercing member.

19. The method of claim 1 wherein the proximal shoulder comprises a sleeve, and wherein a distal end of the sleeve forms the distal contact surface.

20. The method of claim 1 further comprising delivering a contrast agent into the pericardial space to confirm the positioning of the piercing member.

* * * * *